United States Patent
Ito et al.

(10) Patent No.: US 10,981,574 B2
(45) Date of Patent: Apr. 20, 2021

(54) BIOLOGICAL INFORMATION STORAGE SYSTEM AND IN-VEHICLE BIOLOGICAL INFORMATION STORAGE DEVICE

(71) Applicant: Yazaki Corporation, Tokyo (JP)

(72) Inventors: Ken Ito, Shizuoka (JP); Naoto Ishikawa, Shizuoka (JP)

(73) Assignee: YAZAKI CORPORATION, Tokyo (JP)

( * ) Notice: Subject to any disclaimer, the term of this patent is extended or adjusted under 35 U.S.C. 154(b) by 0 days.

(21) Appl. No.: 16/245,419

(22) Filed: Jan. 11, 2019

(65) Prior Publication Data

US 2019/0143991 A1 May 16, 2019

Related U.S. Application Data

(63) Continuation of application No. PCT/JP2017/020618, filed on Jun. 2, 2017.

(30) Foreign Application Priority Data

Jul. 19, 2016 (JP) .............................. JP2016-141176

(51) Int. Cl.
*B60W 40/08* (2012.01)
*A61B 5/00* (2006.01)
(Continued)

(52) U.S. Cl.
CPC ............. *B60W 40/08* (2013.01); *A61B 5/00* (2013.01); *A61B 5/11* (2013.01); *B60R 25/25* (2013.01);
(Continued)

(58) Field of Classification Search
CPC ....................................... B60K 28/06
See application file for complete search history.

(56) References Cited

U.S. PATENT DOCUMENTS

| 2015/0081622 A1* | 3/2015 | Meacham | ............... G06Q 40/04 707/607 |
| 2015/0328985 A1* | 11/2015 | Kim | ..................... B60K 28/066 180/272 |

(Continued)

FOREIGN PATENT DOCUMENTS

| CN | 103340611 A | 10/2013 |
| JP | 2010-057664 A | 3/2010 |

(Continued)

OTHER PUBLICATIONS

Kenney, Briley, "Everything You Need to Know About Internal Storage for Smartwatches," Dec. 30, 2013, Smartwatches.org, pp. 1-3. (Year: 2013).*

(Continued)

*Primary Examiner* — Nabil H Syed
*Assistant Examiner* — Cal J Eustaquio
(74) *Attorney, Agent, or Firm* — Sughrue Mion, PLLC

(57) ABSTRACT

A biological information storage system and an in-vehicle biological information storage device include a biological information detection unit configured to detect biological information of an occupant of a vehicle, an in-vehicle storage unit placed in the vehicle to store information, a portable storage unit provided in a mobile terminal that can be carried to the inside of the vehicle to store information, and an in-vehicle information processing unit capable of executing a processing of distributingly storing the biological information detected by the biological information detection unit in the in-vehicle storage unit and the portable storage unit. In this configuration, the biological information storage system and the in-vehicle biological information storage device can use the biological information inside and outside the vehicle.

4 Claims, 3 Drawing Sheets

(51) Int. Cl.
  *G08G 1/16* (2006.01)
  *A61B 5/11* (2006.01)
  *B60R 25/25* (2013.01)
(52) U.S. Cl.
  CPC ....... *G08G 1/16* (2013.01); *B60W 2040/0872* (2013.01)

(56) References Cited

U.S. PATENT DOCUMENTS

2016/0260264 A1* 9/2016 Shih ................ G07C 5/008
2017/0158202 A1* 6/2017 Yang ................ A61B 5/681

FOREIGN PATENT DOCUMENTS

JP  2012-091570 A  5/2012
JP  2015-203994 A  11/2015

OTHER PUBLICATIONS

Stroud, Forrest, "Server Memory and DiskSpace," Dec. 18, 2013, Webopedia.com, pp. 1-6. (Year: 2011).*
International Search Report for PCT/JP2017/020618, dated Aug. 29, 2017.

* cited by examiner

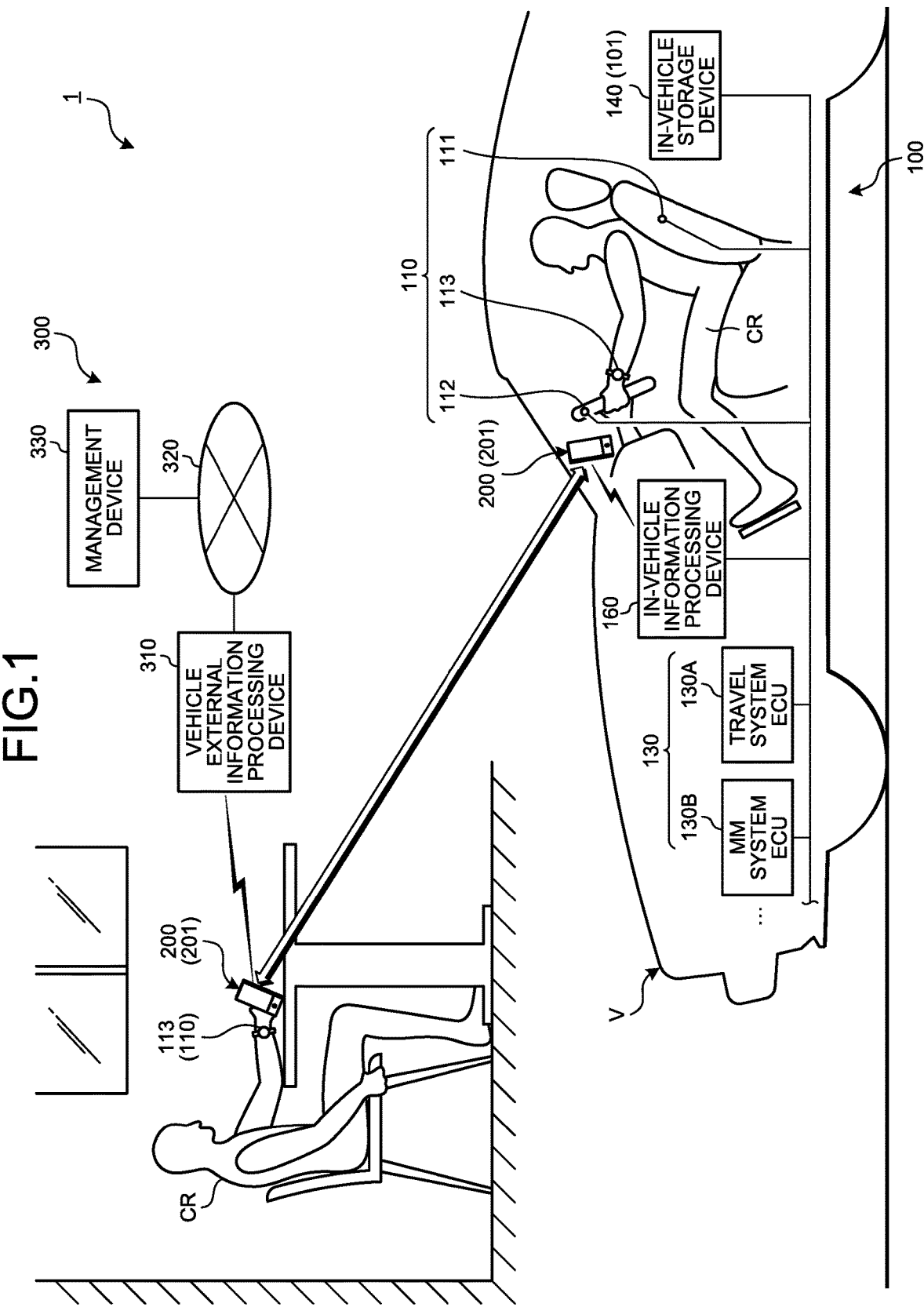

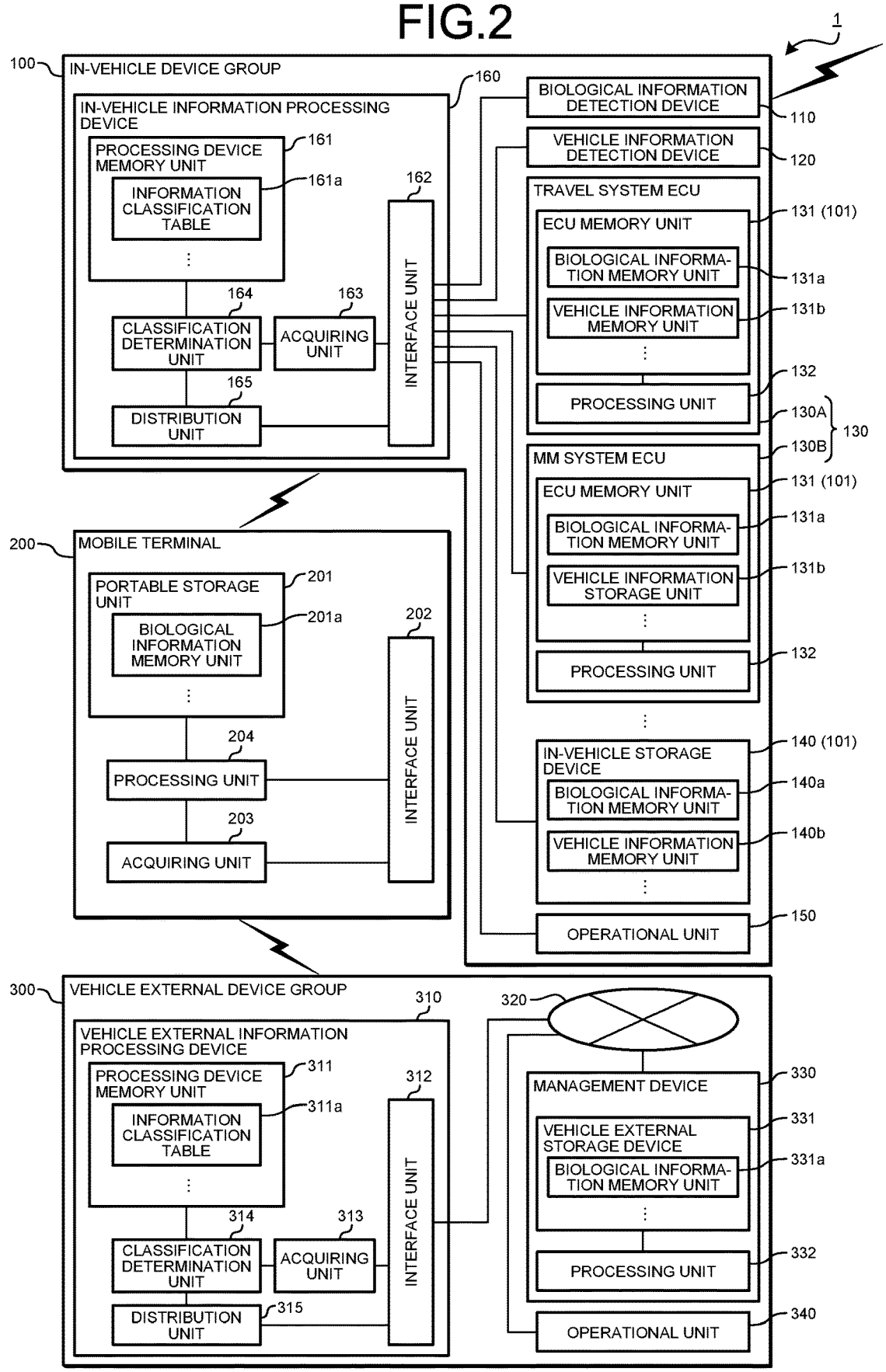

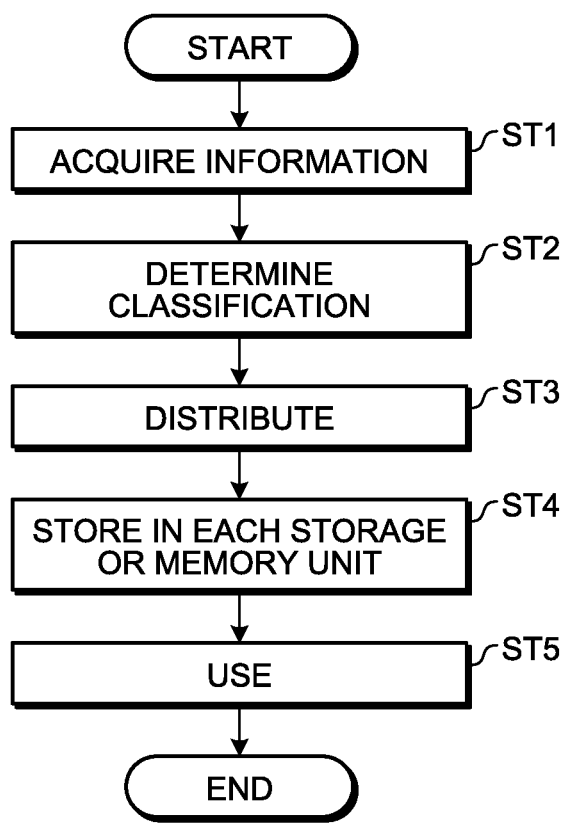

though the present invention will be described by way of an embodiment, the present invention is not limited to the following embodiment. Also, all of the configurations described in the following embodiment are not necessarily indispensable for means for solving the problems of the present invention.

BIOLOGICAL INFORMATION STORAGE SYSTEM AND IN-VEHICLE BIOLOGICAL INFORMATION STORAGE DEVICE

CROSS-REFERENCE TO RELATED APPLICATION(S)

This application is a continuation application of International Application PCT/JP2017/020618, filed on Jun. 2, 2017, and designating the U.S., the entire contents of which are incorporated herein by reference.

BACKGROUND OF THE INVENTION

1. Field of the Invention

The present invention relates to a biological information storage system and an in-vehicle biological information storage device.

2. Description of the Related Art

As a system of the related art that uses biological information in a vehicle, for example, Japanese Patent Application Laid-open No. 2015-203994 discloses a driving assistance device that executes any one of driving assistance operations including an operation of assisting a driver's driving control of the vehicle or an operation of presenting information for the driving control to a driver. This driving assistance device includes a parameter storage unit that stores operation parameters used in the driving assistance operation, a biological information detection unit that detects driver's biological information, a driving behavior detection unit that detects a driver's driving behavior, a condition determination unit that determines a driver's condition on the basis of at least one of the biological information or the driving behavior, a parameter updating unit that changes the operation parameters on the basis of a determination result on the condition, and a driving assistance execution unit that executes a predetermined driving assistance operation depending on the operation parameters.

However, there is a demand for improvement in the driving assistance device of Patent Literature 1 described above, for example, from the viewpoint of use of the biological information.

SUMMARY OF THE INVENTION

In view of the aforementioned problem, the invention provides a biological information storage system and an in-vehicle biological information storage device, capable of using the biological information inside and outside the vehicle.

A biological information storage system according to one aspect of the present invention includes a biological information detection unit configured to detect biological information of an occupant of a vehicle; an in-vehicle storage unit placed in the vehicle to store information; a portable storage unit provided in a mobile terminal that can be carried to the inside of the vehicle to store information; and an in-vehicle information processing unit capable of executing a processing of distributingly storing the biological information detected by the biological information detection unit in the in-vehicle storage unit and the portable storage unit.

According to another aspect of the present invention, in the biological information storage system, the in-vehicle storage unit may include a first storage unit provided in a controller that controls devices of the vehicle and a second storage unit capable of storing information having a capacity larger than that of the first storage unit.

According to still another aspect of the present invention, in the biological information storage system, the biological information detection unit may have a wearable device worn by the occupant and capable of detecting the biological information outside the vehicle, the portable storage unit may store the biological information detected by the wearable device outside the vehicle without using the in-vehicle information processing unit, and the in-vehicle information processing unit may be capable of executing a processing of associating the biological information stored in the portable storage unit and the biological information stored in the in-vehicle storage unit.

According to still another aspect of the present invention, the biological information storage system may further includes a vehicle external storage unit provided outside the vehicle to store information; and a vehicle external information processing unit capable of executing a processing of storing the biological information stored in the portable storage unit in the vehicle external storage unit.

According to still another aspect of the present invention, in the biological information storage system, the vehicle external information processing unit may be capable of executing a processing of associating the biological information stored in the portable storage unit and the biological information stored in the vehicle external storage unit with each other.

According to still another aspect of the present invention, the biological information storage system may further includes an operational unit configured to operate on the basis of current biological information and past biological information.

An in-vehicle biological information storage device according to still another aspect of the present invention includes a biological information detection unit configured to detect biological information of an occupant of a vehicle; an in-vehicle storage unit placed in the vehicle to store information; and an in-vehicle information processing unit capable of executing a processing of distributingly storing the biological information detected by the biological information detection unit in the in-vehicle storage unit and a portable storage unit provided in a mobile terminal that can be carried to the inside of the vehicle to store information.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 1 is a schematic diagram illustrating a schematic configuration of a biological information storage system according to an embodiment;

FIG. 2 is a block diagram illustrating a schematic configuration of the biological information storage system according to an embodiment; and FIG. 3 is a flowchart illustrating an exemplary processing of the biological information storage system according to an embodiment.

DETAILED DESCRIPTION OF THE PREFERRED EMBODIMENTS

Embodiments of the invention will now be described in details with reference to the accompanying drawings. Note that the embodiments are not intended to limit the invention. In addition, in the following embodiments, like reference numerals denote like elements, including those which can be easily replaced by a person ordinarily skilled in the art or are substantially the same as those of the embodiment.

Embodiment

A biological information storage system 1 according to this embodiment illustrated in FIGS. 1 and 2 is a system capable of seamlessly managing and using biological information inside and outside a vehicle V (hereinafter, simply referred to as "inside/outside a vehicle") by distributingly storing biological information of an occupant CR of the vehicle V both in an in-vehicle storage unit 101 inside the vehicle V and a portable storage unit 201 of a mobile terminal 200. Here, the occupant CR of the vehicle V is not limited to a driver of the vehicle V, but may also include a passenger who does not drive the vehicle V. In the following description, a configuration of the biological information storage system 1 will be described in detail with reference to each drawing.

Specifically, the biological information storage system 1 includes an in-vehicle device group 100 provided in the vehicle V, a mobile terminal 200 that can be carried to the inside of the vehicle V, and an external device group 300 provided outside the vehicle V as illustrated in FIGS. 1 and 2. The in-vehicle device group 100 constitutes an in-vehicle biological information storage device. In other words, the mobile terminal 200 can be taken out to the outside of the vehicle V. The external device group 300 constitutes an external biological information storage device. As the mobile terminal 200 cooperates with both the in-vehicle device group 100 and the external device group 300, the biological information storage system 1 causes the in-vehicle device group 100, the mobile terminal 200, and the external device group 300 to cooperate with each other in order to manage and use the biological information of the occupant CR of the vehicle V.

The in-vehicle device group 100 is a device group provided in the vehicle V. The in-vehicle device group 100 includes a biological information detection device 110 as a biological information detection unit, a vehicle information detection device 120, an electronic controller (ECU) 130 as a controller, an in-vehicle storage device 140, an operational unit 150, and an in-vehicle information processing device 160 as an in-vehicle information processing unit. They are provided in the vehicle V.

The biological information detection device 110 detects biological information of the occupant CR of the vehicle V. The biological information of the occupant CR detected by the biological information detection device 110 may include various types of physiological information generated from a living body (occupant CR) and various types of information derived from such information. The biological information of the occupant CR detected by the biological information detection device 110 includes, for example, a vital sign such as electrocardiogram information, a heart rate, a breathing rate, a pulse rate, a blood pressure, a body temperature, a brain wave, and a muscle current, individual identification information for identifying individuals such as fingerprint information, vein information, figure information, voice print information, and iris information, a blood alcohol concentration, eye gaze information, or a sleeping time as derived information estimated from such information, and the like. The biological information detection device 110 has various types of detectors for detecting the information, such as a blood pressure sensor, an electrocardiogram sensor, a heartbeat sensor, a breathing sensor, a pulse sensor, a body temperature sensor, an electroencephalogram sensor, a muscle current sensor, and various individual identification information sensors. The biological information detection device 110 according to this embodiment includes a device capable of detecting the biological information outside the vehicle V in addition to a device capable of detecting the biological information inside the vehicle V. Here, the biological information detection device 110 includes, for example, an in-seat detector 111 provided in a seat of the vehicle V, an in-steering detector 112 provided in a steering of the vehicle V, and a wearable device 113 worn by the occupant CR to detect the biological information outside the vehicle V, and the like. Various types of detectors are provided in the in-seat detector 111, the in-steering detector 112, and the wearable device 113. In addition, the biological information detection device 110 may include various detection devices such as a camera that photographs the occupant CR and detects biological information on the basis of the photographed image or an optical detector that irradiates the occupant CR with light and receives light reflected from the occupant CR to detect biological information on the basis of the reflection light. The biological information detection device 110 is electrically connected to the in-vehicle information processing device 160 and outputs the detected biological information of the occupant CR to the in-vehicle information processing device 160.

The vehicle information detection device 120 detects vehicle information of the vehicle V. The vehicle information detected by the vehicle information detection device 120 is information representing a state of the vehicle V. The vehicle information of the vehicle V detected by the vehicle information detection device 120 may include, for example, a vehicle speed, an acceleration, a steering angle, an accelerator pedal control amount (accelerator depression amount), a brake pedal control amount (brake depression amount) of the vehicle V, whether or not a direction indicator (blinker) is operated and its direction, image information around the vehicle V, external object information around the vehicle V, current position information (GPS information) of the vehicle V, and the like. The vehicle information detection device 120 includes various types of detectors for detecting the above information such as a vehicle speed sensor, an acceleration sensor, a steering angle sensor, an accelerator depression sensor, a brake depression sensor, a blinker switch, an imaging device such as a CCD camera, various radars or sonars, and a GPS receiver. In addition, the vehicle information detection device 120 may be electrically connected to a control device that comprehensively controls the entire vehicle V to detect various types of vehicle information in cooperation with the control device. The vehicle information detection device 120 is electrically connected to the in-vehicle information processing device 160 to output the detected vehicle information of the vehicle V to the in-vehicle information processing device 160.

The ECU 130 is a controller that controls devices inside the vehicle V. The ECU 130 according to this embodiment includes, for example, a travel system ECU 130A and a multimedia (MM) system ECU 130B. However, without limiting thereto, other ECUs may also be included. The travel system ECU 130A controls devices (such as a travel power train, a steering device, and a brake device) relating to a travel control of the vehicle V, an automatic driving control, a safety system control, and the like inside the vehicle V. The MM system ECU 130B controls devices (such as a loudspeaker, an interior illumination, various display devices, and various input/output devices) relating to a multimedia system such as entertainment inside the vehicle V. Note that, in the following description, the travel system ECU 130A and the MM system ECU 130B may be simply referred to as an "ECU 130" unless necessary to distinguish in particular.

Each ECU 130 includes an electronic circuit including, as a main component, a central operation processing unit such as a central processing unit (CPU), a micro processing unit (MPU), an application specific integrated circuit (ASIC), and a field programmable gate array (FPGA), a microcomputer having a read-only memory (ROM), a random access memory (RAM), and an interface well known in the art. Each ECU 130 is electrically connected to the biological information detection device 110, the vehicle information detection device 120, devices inside the vehicle V (such as a travel power train, a steering device, a brake device, a loudspeaker, interior illuminations, various display devices, and various input/output devices) and may transmit or receive various electric signals such as a detection signal corresponding to the detection result or a drive signal for driving each part. Each ECU 130 executes the stored control program on the basis of various input signals to output an output signal to the devices inside the vehicle V and control operations of the devices inside the vehicle V.

Specifically, each ECU 130 includes an ECU memory unit 131 and a processing unit 132 from the viewpoint of a functional concept. The ECU memory unit 131 and the processing unit 132 may transmit/receive various types of information to/from various devices electrically connected.

From the viewpoint of a functional concept, the ECU memory unit 131 includes a biological information memory unit 131a and a vehicle information memory unit 131b. The biological information memory unit 131a is a part for storing biological information in the ECU memory unit 131 of each ECU 130. The biological information memory unit 131a typically stores the biological information detected by the biological information detection device 110 and processed and distributed by the in-vehicle information processing device 160. When the biological information is stored, the biological information memory unit 131a preferably stores essential information such as a detection date/time and a detection position for detecting the information and a storage date/time for storing the information in combination. The vehicle information memory unit 131b is a part for storing vehicle information in the ECU memory unit 131 of each ECU 130. The vehicle information memory unit 131b typically stores vehicle information detected by the vehicle information detection device 120 and processed and distributed by the in-vehicle information processing device 160. When the vehicle information is stored, the vehicle information memory unit 131b preferably stores the essential information in combination. In addition, the ECU memory unit 131 also stores various programs executed by the processing unit 132 or control data.

This ECU memory unit 131 constitutes an in-vehicle storage unit 101 placed in the vehicle V to store information. Here, the in-vehicle storage unit 101 according to this embodiment includes the ECU memory unit 131 and the in-vehicle storage device 140 as a second storage unit described below capable of storing information having a capacity larger than that of the ECU memory unit 131. In addition, the ECU memory unit 131 constitutes a first storage unit of the in-vehicle storage unit 101 provided in each ECU 130 that controls devices inside the vehicle V.

The processing unit 132 comprehensively controls devices inside the vehicle V connected to each ECU 130 (including a travel power train, a steering device, a brake device, loudspeakers, interior illuminations, various display devices, and various input/output devices). The processing unit 132 executes various programs stored in the ECU memory unit 131 and the programs are operated to perform various processings necessary to implement functions of the devices inside the vehicle V.

As described above, the in-vehicle storage device 140 constitutes the in-vehicle storage unit 101 placed in the vehicle V to store information. More specifically, the in-vehicle storage device 140 constitutes a second storage unit capable of storing information having a capacity larger than that of the ECU memory unit 131 in the in-vehicle storage unit 101 as described above. The in-vehicle storage device 140 may include, for example, a relatively large capacity storage device such as a hard disk, a solid state drive (SSD), and an optical disc, or a semiconductor memory capable of rewriting data such as RAM, flash memory, and non-volatile static RAM (NVSRAM). The in-vehicle storage device 140 may constitute a so-called black box which is robustly protected against a strong impact or the like in the vehicle V. The in-vehicle storage device 140 includes a biological information memory unit 140a and a vehicle information memory unit 140b from the viewpoint of a functional concept. The biological information memory unit 140a is a part for storing biological information in the in-vehicle storage device 140. The biological information memory unit 140a typically stores the biological information detected by the biological information detection device 110 and processed and distributed by the in-vehicle information processing device 160. When the biological information is stored, the biological information memory unit 140a preferably stores the essential information in combination. The vehicle information memory unit 140b is a part for storing vehicle information in the in-vehicle storage device 140. The vehicle information memory unit 140b typically stores the vehicle information detected by the vehicle information detection device 120 and processed and distributed by the in-vehicle information processing device 160. When the vehicle information is stored, the vehicle information memory unit 140b preferably stores the essential information in combination.

The operational unit 150 is a device inside the vehicle V operated under control of the ECU 130 or the like and typically controlled by the ECU 130 or the like. More specifically, the operational unit 150 includes devices relating to a travel control for the vehicle V controlled by the travel system ECU 130A, an automatic driving control, and a safety system control, devices relating to a multimedia system such as entertainment controlled by the MM system ECU 130B, and the like. Note that, the operational unit 150 is connected to the ECU 130 or the like via the in-vehicle information processing device 160 in the drawings, but, without limiting thereto, the operational unit 150 may be connected to the ECU 130 or the like without using the in-vehicle information processing device 160.

The in-vehicle information processing device 160 manages and processes various types of information including biological information inside the vehicle V. More specifically, the in-vehicle information processing device 160 has a function of executing a processing of distributingly storing the biological information detected by the biological information detection device 110 in the in-vehicle storage unit 101 (including the ECU memory unit 131 and the in-vehicle storage device 140) and the portable storage unit 201 of the mobile terminal 200, a processing of associating the biological information stored in the portable storage unit 201 and the biological information stored in the in-vehicle storage unit 101 with each other, and the like.

The in-vehicle information processing device 160 includes an electronic circuit having, as a main component, a central operation processing unit such as CPU, MPU, ASIC, and FPGA and a microcomputer having ROM, RAM, and an interface well known in the art. The in-vehicle information processing device 160 is electrically connected to the biological information detection device 110, the vehicle information detection device 120, the ECU 130, the in-vehicle storage device 140, the operational unit 150, and the like to transmit or receive various electric signals such as a detection signal corresponding to the detection result and a drive signal for driving each part. The in-vehicle information processing device 160 executes a stored control program on the basis of various input signals to execute various processings as described above.

Specifically, the in-vehicle information processing device 160 includes a processing device memory unit 161, an interface unit 162, an acquiring unit 163, a classification determination unit 164, and a distribution unit 165 from the viewpoint of a functional concept. The processing device memory unit 161, the interface unit 162, the acquiring unit 163, the classification determination unit 164, and the distribution unit 165 are electrically connected to each other to transmit or receive various types of information.

The processing device memory unit 161 has an information classification table 161a from the viewpoint of a functional concept. The information classification table 161a is an information table regarding classification information for defining classifications of various types of information including the biological information and the vehicle information detected by the biological information detection device 110 and the vehicle information detection device 120. The information classification table 161a is referenced by the classification determination unit 164 when classifications of various types of information are determined. In addition, the processing device memory unit 161 stores various programs or control data executed by the acquiring unit 163, the classification determination unit 164, the distribution unit 165, and the like.

The interface unit 162 is an interface for transmitting/receiving various types of information to/from the biological information detection device 110, the vehicle information detection device 120, the ECU 130, the in-vehicle storage device 140, the operational unit 150, or mobile terminal 200 connected to the in-vehicle information processing device 160. The interface unit 162 has a function of performing a wired or wireless communication control between each part. That is, the interface unit 162 has a function of communicating the information between each part via a communication line or the like in a wired manner and a function of communicating the information between each part via a radio communication unit or the like in a wireless manner. The communication line may include, for example, a dedicated communication line such as a local area network (LAN) cable or a controller area network (CAN) without a limitation. Alternatively, the communication line may include a power line capable of performing power line communication (PLC). The radio communication unit may include, for example, a unit capable of wireless communication of various schemes such as near field communication (NFC) including wireless-LAN (W-LAN), Wi-Fi (registered trademark), Bluetooth (registered trademark), and the like without a limitation. Here, it is assumed that the interface unit 162 is configured such that the biological information detection device 110, the vehicle information detection device 120, the ECU 130, the in-vehicle storage device 140, and the operational unit 150 are connected in a wired manner, and the mobile terminal 200 is connected in a wireless manner. However, without limiting thereto, the vehicle information detection device 120, the ECU 130, the in-vehicle storage device 140, and the operational unit 150 may be connected in a wireless manner, and the mobile terminal 200 may be connected in a wired manner.

The acquiring unit 163, the classification determination unit 164, and the distribution unit 165 are parts for executing various processings in the in-vehicle information processing device 160. The acquiring unit 163, the classification determination unit 164, and the distribution unit 165 execute various programs stored in the processing device memory unit 161. As the program is operated, various processings necessary to manage or process various types of information including the biological information inside the vehicle V are performed.

The acquiring unit 163 is a part for executing a processing of acquiring various types of information. The acquiring unit 163 acquires various types of information such as the biological information and the vehicle information via the interface unit 162 from the biological information detection device 110, the vehicle information detection device 120, the ECU 130, the in-vehicle storage device 140, the operational unit 150, the mobile terminal 200, and the like. The acquiring unit 163 may store the acquired information in the processing device memory unit 161.

The classification determination unit 164 is a part for executing a processing of determining classifications of various types of information acquired by the acquiring unit 163. The classification determination unit 164 determines the classification of the information acquired by the acquiring unit 163 on the basis of the information classification table 161a by referencing the information classification table 161a stored in the processing device memory unit 161.

The distribution unit 165 is a part for executing a processing of distributingly storing the biological information, the vehicle information, and the like detected by the biological information detection device 110 and the vehicle information detection device 120 and acquired by the acquiring unit 163 in the in-vehicle storage unit 101 (including the ECU memory unit 131 and in-vehicle storage device 140) and the portable storage unit 201 of the mobile terminal 200. In addition, the distribution unit 165 may also execute a processing of storing the biological information from the mobile terminal 200 acquired by the acquiring unit 163 in the in-vehicle storage unit 101. In some cases, the distribution unit 165 sorts the biological information from the mobile terminal 200 acquired by the acquiring unit 163 and stores the information in the in-vehicle storage unit 101. As a result, the distribution unit 165 can execute a processing of associating the biological information stored in the portable storage unit 201 and the biological information stored in the in-vehicle storage unit 101 with each other. Here, since the in-vehicle storage unit 101 has the ECU memory unit 131 and the in-vehicle storage device 140, the distribution unit 165 distributes the biological information acquired by the acquiring unit 163 to the ECU memory unit 131, the in-vehicle storage device 140, and the portable storage unit 201. Furthermore, the distribution unit 165 distributingly stores the biological information in the ECU memory unit 131 of the travel system ECU 130A, the ECU memory unit 131 of the MM system ECU 130B, the in-vehicle storage device 140, and the portable storage unit 201. The distribution unit 165 sorts and distributes the biological information acquired by the acquiring unit 163 on the basis of the classification of the information determined by the classification determination unit 164 and stores the information in the biological information memory units 131a and 140a, and the biological information memory unit 201a, which is described below, of the ECU memory unit 131, the in-vehicle storage device 140, and the portable storage unit 201. Similarly, the distribution unit 165 sorts and distributes the vehicle information acquired by the acquiring unit 163 on the basis of the classifications of the information determined by the classification determination unit 164 and stores the information in the vehicle information memory units 131b and 140b of the ECU memory unit 131 and the in-vehicle storage device 140. Note that an example of the information distribution will be described below in details.

The mobile terminal 200 is a device that stores the biological information in cooperation with both the in-vehicle device group 100 and the external device group 300 to associate the in-vehicle device group 100, the mobile terminal 200, and the external device group 300 with each other. The mobile terminal 200 has a function of executing a processing of storing the biological information processed and distributed by the in-vehicle information processing device 160 or a vehicle external information processing device 310 described below and a processing of storing the biological information detected by the biological information detection device 110 outside the vehicle V without using the in-vehicle information processing device 160 or the like. The mobile terminal 200 may include, for example, a mobile phone, a smart phone, a PHS, a PDA, a tablet personal computer (PC), a notebook PC, a wearable terminal, and the like.

The mobile terminal 200 includes an electronic circuit having, as a main component, a central operation processing unit such as CPU, MPU, ASIC, and FPGA and a microcomputer having ROM, RAM, and an interface well known in the art. The mobile terminal 200 executes a stored control program on the basis of various input signals or the like to execute various processings as described above.

Specifically, the mobile terminal 200 includes a portable storage unit 201, an interface unit 202, an acquiring unit 203, and a processing unit 204 from the viewpoint of a functional concept. The portable storage unit 201, the interface unit 202, the acquiring unit 203, and the processing unit 204 are electrically connected to each other to transmit or receive various types of information.

The portable storage unit 201 includes the biological information memory unit 201a. The biological information memory unit 201a is a part for storing the biological information in the portable storage unit 201 of the mobile terminal 200. The biological information memory unit 201a typically stores the biological information detected by the biological information detection device 110 and processed and distributed by the in-vehicle information processing device 160 or the vehicle external information processing device 310 described below. In addition, the biological information memory unit 201a may store the biological information detected by the biological information detection device 110 outside the vehicle V, for example, the wearable device 113 without using the in-vehicle information processing device 160, the vehicle external information processing device 310, or the like. The biological information memory unit 201a preferably stores the essential information in combination when the biological information is stored. In addition, the portable storage unit 201 stores various programs or control data executed by the acquiring unit 203 or the processing unit 204.

The interface unit 202 is an interface for transmitting/receiving various types of information to/from the in-vehicle information processing device 160, the vehicle external information processing device 310 described below, and the like. That is, the interface unit 202 has a function of communicating information with each part via a communication line or the like in a wired manner and a function of communicating the information with each part via a radio communication unit in a wireless manner. The communication line may be a dedicated communication line electrically connected to the interface unit 202 via various types of connectors such as a LAN cable or CAN without a limitation. Alternatively, the communication line may include a power line capable of performing power line communication. The radio communication unit may include, for example, a unit capable of wireless communication of various schemes such as near field communication (NFC) including wireless-LAN (W-LAN), Wi-Fi (registered trademark), Bluetooth (registered trademark), and the like without a limitation.

The acquiring unit 203 and the processing unit 204 are parts for executing various processings in the mobile terminal 200. The acquiring unit 203 and the processing unit 204 execute various programs stored in the portable storage unit 201. As the program is operated, various processings necessary to manage or process various types of information including the biological information inside and outside the vehicle V are performed.

The acquiring unit 203 is a part for executing a processing for acquiring various types of information. The acquiring unit 203 acquires various types of information such as the biological information via the interface unit 20 from the in-vehicle information processing device 160, the vehicle external information processing device 310 described below, and the like. In addition, the acquiring unit 203 may acquire the biological information detected by the biological information detection device 110 outside the vehicle V, such as the wearable device 113 via the interface unit 202 without using the in-vehicle information processing device 160, the vehicle external information processing device 310 described below, or the like. The acquiring unit 203 may store the acquired information in the portable storage unit 201.

The processing unit 204 is a part for comprehensively controlling the mobile terminal 200. The processing unit 204 may execute a processing of storing the biological information or the like detected by the biological information detection device 110, processed and distributed by the in-vehicle information processing device 160 or the vehicle external information processing device 310 described below, and acquired by the acquiring unit 203 in the biological information memory unit 201a of the portable storage unit 201. In addition, the processing unit 204 may also execute a processing of storing the biological information detected by the biological information detection device 110 outside the vehicle V and acquired by the acquiring unit 203 directly in the biological information memory unit 201a of the portable storage unit 201 without using the in-vehicle information processing device 160 or the vehicle external information processing device 310 described below.

The external device group 300 is a device group provided outside the vehicle V, such as in a house. The external device group 300 has an vehicle external information processing device 310 as a vehicle external information processing unit, a network 320, a management device 330, and an operational unit 340 provided outside the vehicle V. Here, it is assumed that the external device group 300 is configured such that the vehicle external information processing device 310, the management device 330, and the operational unit 340 are connected via the network 320, and the management device 330 and the operational unit 340 are embedded as a so-called cloud. Note that the external device group 300 may be configured such that the vehicle external information processing device 310, the management device 330, and the operational unit 340 are connected without using the network 320, and these may be combined as a so-called standalone type device. The external device group 300 may also be configured by installing applications capable of implementing various processings described below in a computer system such as an existing PC or a workstation.

The vehicle external information processing device 310 manages and processes various types of information including biological information outside the vehicle V. More specifically, the vehicle external information processing device 310 has a function of executing a processing of storing the biological information stored in the portable storage unit 201 in the vehicle external storage device 331 as a vehicle external storage unit, a processing of associating the biological information stored in the portable storage unit 201 and the biological information stored in the vehicle external storage device 331, and the like.

The vehicle external information processing device 310 includes an electronic circuit having, as a main component, a central operation processing unit such as CPU, MPU, ASIC, and FPGA and a microcomputer having ROM, RAM, and an interface well known in the art. The vehicle external information processing device 310 may be electrically connected to the management device 330, the operational unit 340, and the like via the network 320 to transmit or receive various electric signals. The vehicle external information processing device 310 executes a stored control program on the basis of various input signals or the like to execute various processings as described above.

Specifically, the vehicle external information processing device 310 includes a processing device memory unit 311, an interface unit 312, an acquiring unit 313, a classification determination unit 314, and a distribution unit 315 from the viewpoint of a functional concept. The processing device memory unit 311, the interface unit 312, the acquiring unit 313, the classification determination unit 314, and the distribution unit 315 are electrically connected to each other to transmit or receive various types of information.

The processing device memory unit 311 has an information classification table 311a from the viewpoint of a functional concept. The information classification table 311a is an information table regarding classification information for determining classifications of various types of information including the biological information acquired from the mobile terminal 200 or the like. The information classification table 311a is referenced when the classification determination unit 314 determines the classifications of various types of information. In addition, the processing device memory unit 311 stores various programs or control data executed by the acquiring unit 313, the classification determination unit 314, the distribution unit 315, or the like.

The interface unit 312 is an interface for transmitting/receiving various types of information to/from the management device 330, the operational unit 340, the mobile terminal 200, or the like connected to the vehicle external information processing device 310 via the network 320. The interface unit 312 has a function of performing a wired or wireless communication control between each part. That is, the interface unit 312 has a function of communicating the information between each part via a communication line or the like in a wired manner and a function of communicating the information between each part via a radio communication unit or the like in a wireless manner. The communication line may include, for example, a dedicated communication line such as a LAN cable or CAN without a limitation. Alternatively, the communication line may include a power line capable of performing power line communication. The radio communication unit may include, for example, a unit capable of wireless communication of various schemes such as near field communication (NFC) including W-LAN, Wi-Fi (registered trademark), Bluetooth (registered trademark), and the like without a limitation.

The acquiring unit 313 is a part for executing a processing of acquiring various types of information. The acquiring unit 313 acquires various types of information such as the biological information via the interface unit 312 from the management device 330, the operational unit 340, the mobile terminal 200, and the like. The acquiring unit 313 may store the acquired information in the processing device memory unit 311.

The classification determination unit 314 is a part for executing a processing of determining the classifications of various types of information acquired by the acquiring unit 313. The classification determination unit 314 determines the classification of the information acquired by the acquiring unit 313 on the basis of the information classification table 311a by referencing the information classification table 311a stored in the processing device memory unit 311.

The distribution unit 315 is a part for executing a processing of storing the biological information or the like stored in the portable storage unit 201 and acquired by the acquiring unit 313 from the portable storage unit 201 in a vehicle external storage device 331 described below. In some cases, the distribution unit 315 sorts the biological information from the portable storage unit 201 of the mobile terminal 200 acquired by the acquiring unit 313 and stores the information in the vehicle external storage device 331. In addition, the distribution unit 315 may execute a processing of associating the biological information stored in the portable storage unit 201 and the biological information stored in the vehicle external storage device 331 or the like. The distribution unit 315 sorts and distributes the biological information acquired by the acquiring unit 313 on the basis of the classification of the information determined by the classification determination unit 314 and stores the information in the biological information memory unit 331a of the vehicle external storage device 331 described below.

The network 320 is used to communicatably connect the vehicle external information processing device 310, the management device 330, and the operational unit 340. The network 320 makes it possible to exchange various types of information including the biological information between the vehicle external information processing device 310, the management device 330, and the operational unit 340. The network 320 may include any communication network such as LAN or virtual private network (VPN) regardless of a wired or wireless scheme.

The management device 330 provides various services based on the biological information. The management device 330 includes an electronic circuit having, as a main component, a central operation processing unit such as CPU, MPU, ASIC, and FPGA and a microcomputer having ROM, RAM, and an interface well known in the art. The management device 330 may be electrically connected to the vehicle external information processing device 310, the operational unit 340, and the like via the network 320 to transmit or receive various electric signals. The management device 330 executes the stored control program on the basis of various input signals or the like to execute various processings regarding various services. Furthermore, the management device 330 outputs an output signal to the operational unit 340 or the like on the basis of various input signals to control the operation of the operational unit 340.

Specifically, the management device 330 includes a vehicle external storage device 331 as a vehicle external storage unit and a processing unit 332 from the viewpoint of a functional concept. The vehicle external storage device 331 and the processing unit 332 may transmit/receive various types of information to/from various devices electrically connected.

The vehicle external storage device 331 is a so-called server device provided outside the vehicle V to store information. The vehicle external storage device 331 may include, for example, a relatively large capacity storage device such as a hard disk, SSD, and an optical disc, or a semiconductor memory capable of rewriting data such as RAM, flash memory, and NVSRAM. The vehicle external storage device 331 includes a biological information memory unit 331a from the viewpoint of a functional concept. The biological information memory unit 331a is a part for storing the biological information in the vehicle external storage device 331. The biological information memory unit 331a typically stores the biological information processed and distributed by the vehicle external information processing device 310. The biological information memory unit 331a preferably stores the essential information in combination when the biological information is stored. In addition, the vehicle external storage device 331 also stores various programs executed by the processing unit 332 or control data.

The processing unit 332 is a part for comprehensively controlling the operational unit 340 connected to the management device 330 via the network 320. The processing unit 332 performs various processings necessary to execute various programs stored in the vehicle external storage device 331 and implement the function of the operational unit 340 as the program is operated.

The operational unit 340 is operated under control of the management device 330 or the like and is typically a device for implementing various services provided by the management device 330 or the like. The operational unit 340 includes a device relating to various services provided by the management device 330 or the like, such as a loudspeaker, various display devices, and various input/output devices.

Next, an exemplary control flow of the biological information storage system 1 will be described with reference to the flowchart of FIG. 3. Here, the description will be made by focusing on distribution of the biological information in the in-vehicle information processing device 160 and the vehicle external information processing device 310. Furthermore, here, the processing of the in-vehicle information processing device 160 and the processing of the vehicle external information processing device 310 will be commonly described in combination as long as possible.

First, the acquiring units 163 and 313 of the in-vehicle information processing device 160 and the vehicle external information processing device 310 acquire various types of information such as the biological information and the vehicle information via the interface units 162 and 312 as an information acquiring process (Step ST1). In this case, the acquiring unit 163 of the in-vehicle information processing device 160 acquires various types of information such as the biological information and the vehicle information via the interface unit 162 from the biological information detection device 110, the vehicle information detection device 120, the in-vehicle storage device 140, the mobile terminal 200, and the like. The acquiring unit 313 of the vehicle external information processing device 310 acquires various types of information such as the biological information via the interface unit 312 from the management device 330, the mobile terminal 200, and the like.

Then, the classification determination units 164 and 314 of the in-vehicle information processing device 160 and the vehicle external information processing device 310 determine the classifications of the biological information and the vehicle information acquired by the acquiring units 163 and 313 in Step ST1 on the basis of the information classification tables 161a and 311a stored in the processing device memory units 161 and 311 by referencing the information classification tables 161a and 311a as a classification determination process (Step ST2).

Then, the distribution units 165 and 315 of the in-vehicle information processing device 160 and the vehicle external information processing device 310 distribute the biological information and the vehicle information acquired by the acquiring units 163 and 313 in Step ST1 depending on the classification of the information determined in Step ST2 to the ECU memory unit 131, the in-vehicle storage device 140, the portable storage unit 201, and the vehicle external storage device 331 as a distribution process (Step ST3) and stores the information in each storage or memory unit as a storing process (Step ST4). In this case, the distribution unit 165 sorts and distributes the biological information acquired by the acquiring unit 163 depending on the classification and stores the information in the biological information memory units 131a, 140a, and 201a of the ECU memory unit 131 (including the travel system ECU 130A and the MM system ECU 130B), the in-vehicle storage device 140, and the portable storage unit 201. As a result, the distribution unit 165 associates the biological information stored in the portable storage unit 201, the biological information stored in the ECU memory unit 131, and the biological information stored in the in-vehicle storage device 140 with each other. Similarly, the distribution unit 165 may sort and distribute the vehicle information acquired by the acquiring unit 163 depending on the classification and store the information in the biological information memory units 131a and 140a of the ECU memory unit 131 (including the travel system ECU 130A and the MM system ECU 130B) and the in-vehicle storage device 140. Meanwhile, the distribution unit 315 sorts and distributes the biological information acquired by the acquiring unit 313 and stores the information in the biological information memory units 331a and 201a of the vehicle external storage device 331 and the portable storage unit 201. As a result, the distribution unit 165 can associate the biological information stored in the portable storage unit 201 and the biological information stored in the vehicle external storage device 331 with each other.

The biological information storage system 1 completes this control flow as the biological information and the vehicle information are distributed and stored in each storage or memory unit such as the ECU memory unit 131, the in-vehicle storage device 140, the portable storage unit 201, and the vehicle external storage device 331, and the biological information or the vehicle information stored in each storage or memory unit becomes available in the operational unit 150 or 340 (Step ST5).

Next, specific operations of the biological information storage system 1 configured as described above will be described.

When the biological information stored in the portable storage unit 201, the biological information stored in the ECU memory unit 131, and the biological information stored in the in-vehicle storage device 140 are associated with each other, the biological information storage system 1 may match all pieces of the biological information stored in each storage or memory unit or associate the information by sorting a part of them depending on use purposes. Similarly, when the biological information stored in the portable storage unit 201 and the biological information stored in the vehicle external storage device 331 are associated with each other, the biological information storage system 1 may match all pieces of the biological information stored in each storage or memory unit or may associate the information by sorting a part of them depending on use purposes. For example, since the in-vehicle storage device 140 and the vehicle external storage device 331 are relatively large capacity storages, in principle, all pieces of biological information detected by the biological information detection device 110 may be stored to make a database. Meanwhile, the ECU memory unit 131 may store, for example, the biological information used for operating the operational unit 150 or the like by limiting the range. In addition, for example, the in-vehicle storage device 140 may store the biological information used in a plurality of ECUs 130 (in this case, both the travel system ECU 130A and the MM system ECU 130B), and the ECU memory unit 131 of each ECU 130 may store only the biological information used individually. Furthermore, in a case where the in-vehicle storage device 140 is configured as a black box that is robustly protected against a strong impact or the like in the vehicle V, the biological information and the vehicle information may be stored in association with each other in order to use them in verification of a traffic accident, or a survey of accident factors, and the like. The portable storage unit 201 may store all pieces of the biological information detected by the biological information detection device 110 in order to cause the in-vehicle storage device 140 and the vehicle external storage device 331 to cooperate with each other or may store any type of biological information by limiting the range depending on a user's demand or the like.

The biological information storage system 1 may, for example, sequentially accumulate the biological information stored in the ECU memory unit 131, the in-vehicle storage device 140, the portable storage unit 201, and the vehicle external storage device 331 as described above or may update the biological information frequently on a predetermined update timing basis. For example, since the in-vehicle storage device 140 and the vehicle external storage device 331 are relatively large capacity storages, in principle, all pieces of the biological information distributed and stored by the distribution units 165 and 315 may be stored in a time series manner and may be cleared (deleted) in response to a predetermined operation made using various input/output devices depending on a user's demand or the like. Meanwhile, for example, in a case where only the biological information for a relatively short time period used to operate the operational unit 150 or the like is needed, the ECU memory unit 131 may update the biological information frequently on a predetermined update timing basis. Furthermore, the portable storage unit 201 may be set to select, for example, whether all pieces of the biological information are stored or whether the biological information is updated on a predetermined update timing basis depending on a user's demand or the like.

In the biological information storage system 1, the operational units 150 and 340 are operated on the basis of the biological information stored in the ECU memory unit 131, the in-vehicle storage device 140, the portable storage unit 201, and the vehicle external storage device 331 as described above. Each operational unit 150 and 340 may be operated on the basis of the current biological information and the past biological information stored in the ECU memory unit 131, the in-vehicle storage device 140, the portable storage unit 201, and the vehicle external storage device 331. More specifically, the operational unit 150 may be operated on the basis of the biological information detected from the outside of the vehicle V in addition to the biological information detected from the inside of the vehicle V. Reversely, the operational unit 340 may be operated on the basis of the biological information detected from the inside of the vehicle V in addition to the biological information detected from the outside of the vehicle V.

For example, the operational unit 150 provided in the vehicle V may check a blood alcohol concentration of an occupant CR on the basis of the current biological information stored in the ECU memory unit 131, the in-vehicle storage device 140, the portable storage unit 201, and the like, and output the blood alcohol concentration via various display devices or various input/output devices under control of the ECU 130 to notify the occupant CR.

For example, the operational unit 150 provided in the vehicle V may estimate a driver's fatigue level and arousal level among the occupants CR on the basis of the past biological information (for example, the sleeping hours in the last several days or the like) in addition to the current biological information stored in the ECU memory unit 131, the in-vehicle storage device 140, the portable storage unit 201, and the like, and output the fatigue level and arousal level via various display devices, various input/output devices, and the like under control of the ECU 130 to notify the occupant CR in order to urge a driving stop or a driver change.

For example, the operational unit 150 provided in the vehicle V may obtain a difference between the current biological information and the past biological information stored in the ECU memory unit 131, the in-vehicle storage device 140, the portable storage unit 201, and the like to check a more specific current condition of the occupant CR, and output this specific condition via various display devices, various input/output devices, and the like under control of the ECU 130 to notify the occupant CR.

For example, the operational unit 150 provided in the vehicle V may automatically adjust devices relating to a multimedia system (such as a loudspeaker, an interior illumination, various display devices, and various input/output devices) to match the current condition or the like under control of the ECU 130 on the basis of the biological information stored in the ECU memory unit 131, the in-vehicle storage device 140, the portable storage unit 201, and the like, or may automatically adjust devices relating to a travel control of the vehicle V, an automatic driving control, a safety system control, or the like (such as a travel power train, a steering device, and a brake device).

For example, the operational unit 340 provided outside the vehicle V may check a specific heath condition of the occupant CR on the basis of the current biological information and the past biological information stored in the portable storage unit 201, the vehicle external storage device 331, and the like and output an advice based on the health condition, a health care schedule, and the like via various display devices, various input/output devices, and the like under control of the management device 330 to notify the occupant CR so as to perform health management.

The biological information storage system 1 described above includes the biological information detection device 110 that detects the biological information of the occupant CR of the vehicle V, the in-vehicle storage unit 101 placed in the vehicle V to store information, the portable storage unit 201 provided in a mobile terminal 200 that can be carried to the inside of the vehicle V to store information, and an in-vehicle information processing device 160 capable of executing a processing of distributingly storing the biological information detected by the biological information detection device 110 in the in-vehicle storage unit 101 and the portable storage unit 201.

The in-vehicle device group 100 described above includes the biological information detection device 110 that detects biological information of the occupant CR of the vehicle V, the in-vehicle storage unit 101 placed in the vehicle V to store information, and an in-vehicle information processing device 160 capable of executing a processing of distributingly storing the biological information detected by the biological information detection device 110 in the in-vehicle storage unit 101 and the portable storage unit 201 provided in the mobile terminal 200 that can be carried to the inside of the vehicle V to store information.

Therefore, since the biological information storage system 1 and the in-vehicle device group 100 distributingly store the biological information of the occupant CR of the vehicle V detected by the biological information detection device 110 in the in-vehicle storage unit 101 and the portable storage unit 201 using the in-vehicle information processing device 160, the inside of the vehicle V may use the biological information stored in the in-vehicle storage unit 101, and the outside of the vehicle V may use the biological information stored in the portable storage unit 201 provided in the mobile terminal 200. As a result, the biological information storage system 1 and the in-vehicle device group 100 can seamlessly manage and use the biological information of the occupant CR of the vehicle V inside and outside of the vehicle V. Therefore, it is possible to appropriately use the biological information inside and outside the vehicle.

In the biological information storage system 1 and the in-vehicle device group 100 described above, the in-vehicle storage unit 101 includes the ECU memory unit 131 provided in the ECU 130 that controls devices inside the vehicle V, and the in-vehicle storage device 140 capable of storing information having a capacity larger than that of the ECU memory unit 131. Therefore, the biological information storage system 1 and the in-vehicle device group 100 can distributingly store the biological information of the occupant CR of the vehicle V in the ECU memory unit 131 and the in-vehicle storage device 140 depending on the use purpose, the classification, and the like inside the vehicle V. Therefore, it is possible to more diversely classify and use the biological information stored in the ECU memory unit 131 and in-vehicle storage device 140.

In the biological information storage system 1 and the in-vehicle device group 100 described above, the biological information detection device 110 includes the wearable device 113 worn by the occupant CR to detect the biological information outside the vehicle V, and the portable storage unit 201 stores the biological information detected by the wearable device 113 outside the vehicle V without using the in-vehicle information processing device 160. In addition, the in-vehicle information processing device 160 may execute a processing of associating the biological information stored in the portable storage unit 201 and the biological information stored in the in-vehicle storage unit 101 with each other. Therefore, the biological information storage system 1 and the in-vehicle device group 100 can manage and use the biological information of the occupant CR detected outside the vehicle V in addition to the biological information of the occupant CR detected inside the vehicle V together. Therefore, it is possible to more appropriately use the biological information inside and outside the vehicle.

The biological information storage system 1 described above has the vehicle external storage device 331 provided outside the vehicle V to store information and the vehicle external information processing device 310 capable of executing a processing of storing the biological information stored in the portable storage unit 201 in the vehicle external storage device 331. More specifically, in the biological information storage system 1 described above, the vehicle external information processing device 310 can execute a processing of associating the biological information stored in the portable storage unit 201 and the biological information stored in the vehicle external storage device 331. Therefore, in the biological information storage system 1, the portable storage unit 201 of the mobile terminal 200 cooperates with both the in-vehicle storage unit 101 and the vehicle external storage device 331 through a processing of the vehicle external information processing device 310. As a result, it is possible to manage and use the biological information of the occupant CR of the vehicle V in cooperation with the in-vehicle storage unit 101, the portable storage unit 201, and the vehicle external storage device 331.

The biological information storage system 1 and the in-vehicle device group 100 described above have the operational units 150 and 340 operated on the basis of the current biological information and the past biological information. Therefore, the biological information storage system 1 and the in-vehicle device group 100 can operate the operational units 150 and 340 on the basis of the biological information of the occupant CR having higher accuracy based on the current biological information and the past biological information.

Note that the biological information storage system and the in-vehicle biological information storage device described above according to an embodiment of the invention are not limited to the aforementioned embodiments, and various modifications can be made within the scope described in claims.

The information classification tables 161a and 311a, the programs, the control data, the applications, and the like described above may be updated appropriately or may be stored in a server connected to the in-vehicle device group 100, the mobile terminal 200, and the external device group 300 via any network. For example, they may be downloaded entirely or partially as necessary. In addition, the processing functions of each device of the in-vehicle device group 100, the mobile terminal 200, and the external device group 300 may be implemented entirely or partially, for example, by a CPU or a program analyzed and executed on the CPU. Alternatively, the functions may be implemented as hardware such as a wired logic connection.

In the aforementioned description, the biological information detection device 110 is included in the in-vehicle device group 100. However, as described above, a part of the devices such as the wearable device 113 may be taken out from the vehicle V. In addition, the biological information detection device 110 includes the wearable device 113 that detects the biological information outside the vehicle V in addition to the device that detects biological information inside the vehicle V. However, without limiting thereto, the biological information detection device 110 may not have the wearable device 113. Furthermore, the external device group 300 of the biological information storage system 1 may also have the biological information detection device similar to the biological information detection device 110.

In the aforementioned description, the biological information storage system 1 includes the external device group 300. However, without limiting thereto, the external device group 300 may not be provided.

In the aforementioned description, the in-vehicle storage unit 101 includes the ECU memory unit 131 as a first storage unit and the in-vehicle storage device 140 as a second storage unit. However, without limiting thereto, any one of the first and second storage units may be omitted.

Note that, for example, in a case where a plurality of mobile terminals 200 are used, the biological information storage system 1 may associate the individual identification information of each mobile terminal 200 and the individual identification information contained in the biological information of the occupants CR who own the mobile terminals 200 with each other in advance in order to specify a corresponding combination of the mobile terminal 200 and the occupant CR in advance. In addition, the in-vehicle information processing device 160 and the vehicle external information processing device 310 may appropriately distribute the biological information depending on this combination.

The biological information storage system and the in-vehicle biological information storage device according to the embodiments distributingly store biological information of an occupant of a vehicle detected by the biological information detection unit in the in-vehicle storage unit and the portable storage unit using the in-vehicle information processing unit. The biological information stored in the in-vehicle storage unit can be used inside the vehicle, and the biological information stored in the portable storage unit provided in the mobile terminal can be used outside the vehicle. Therefore, it is possible to use the biological information inside and outside the vehicle.

Although the invention has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A biological information storage system comprising:
   a biological information detection unit configured to detect biological information of an occupant of a vehicle;
   an in-vehicle storage unit placed in the vehicle to store information;
   a portable storage unit provided in a mobile terminal that can be carried to the inside of the vehicle to store information; and
   an in-vehicle information processing unit configured to execute a processing of distributingly storing the biological information detected by the biological information detection unit in the in-vehicle storage unit and the portable storage unit depending on a classification of the biological information, wherein
   the biological information concerns health management information, and is at least one vital sign selected from the group consisting of electrocardiogram information, a heart rate, a breathing rate, a pulse rate, a blood pressure, a body temperature, a brain wave, and a muscle current; a blood alcohol concentration; eye gaze information; or a sleeping time as derived information estimated from such information,
   the portable storage unit stores the biological information detected outside the vehicle without using the in-vehicle information processing unit, and
   the in-vehicle information processing unit is configured to execute a processing of associating the biological information stored in the portable storage unit and the biological information stored in the in-vehicle storage unit.

2. The biological information storage system according to claim 1, further comprising:
   a vehicle external storage unit provided outside the vehicle to store information; and
   a vehicle external information processing unit configured to execute a processing of storing the biological information stored in the portable storage unit in the vehicle external storage unit.

3. The biological information storage system according to claim 1, further comprising:
   an operational unit configured to operate on the basis of current biological information and past biological information.

4. An in-vehicle biological information storage device comprising:
   a biological information detection unit configured to detect biological information of an occupant of a vehicle;
   an in-vehicle storage unit placed in the vehicle to store information; and
   an in-vehicle information processing unit configured to execute a processing of distributingly storing the biological information detected by the biological information detection unit in the in-vehicle storage unit and a portable storage unit provided in a mobile terminal that can be carried to the inside of the vehicle to store information depending on a classification of the biological information, wherein
   the biological information concerns health management information, and is at least one vital sign selected from the group consisting of electrocardiogram information, a heart rate, a breathing rate, a pulse rate, a blood pressure, a body temperature, a brain wave, and a muscle current; a blood alcohol concentration; eye gaze information; or a sleeping time as derived information estimated from such information,
   the portable storage unit stores the biological information detected outside the vehicle without using the in-vehicle information processing unit, and
   the in-vehicle information processing unit is configured to execute a processing of associating the biological information stored in the portable storage unit and the biological information stored in the in-vehicle storage unit.

* * * * *